(12) United States Patent
Deaton et al.

(10) Patent No.: US 12,653,847 B2
(45) Date of Patent: *Jun. 16, 2026

(54) BACILLUS SUBTILIS PROBIOTICS AND METHODS OF USE FOR IMPROVING IMMUNE FUNCTION, HORMONAL STATUS, AND PHYSICAL PERFORMANCE

(71) Applicant: Deerland Enzymes, Inc., Kennesaw, GA (US)

(72) Inventors: John Deaton, Kennesaw, GA (US); Ana Maria Cuentas, Woodstock, GA (US)

(73) Assignee: Deerland Enzymes, Inc., Kennesaw, GA (US)

( * ) Notice: Subject to any disclaimer, the term of this patent is extended or adjusted under 35 U.S.C. 154(b) by 171 days.

This patent is subject to a terminal disclaimer.

(21) Appl. No.: 18/508,430

(22) Filed: Nov. 14, 2023

(65) Prior Publication Data

US 2024/0075078 A1     Mar. 7, 2024

Related U.S. Application Data

(63) Continuation-in-part of application No. 16/593,469, filed on Oct. 4, 2019, now Pat. No. 11,813,296.

(60) Provisional application No. 62/741,300, filed on Oct. 4, 2018.

(51) Int. Cl.
*A61K 35/742* (2015.01)
*C12R 1/125* (2006.01)

(52) U.S. Cl.
CPC ...... *A61K 35/742* (2013.01); *C12R 2001/125* (2021.05)

(58) Field of Classification Search
None
See application file for complete search history.

(56) References Cited

U.S. PATENT DOCUMENTS 9,138,441 B2     9/2015   Trachtman

OTHER PUBLICATIONS

Chen, Y-M, et al., "Lactobacillus plantarum TWK10 supplementation improves exercise performance and increases muscle mass in mice," Nutrients 8: 205, 2016.
Chicharro, J.L., et al., "Saliva composition and exercise," Sports medicine 26: 17-27, 1998 (Abstract Only).
Clancy, R.L., et al., "Reversal in fatigued athletes of a defect in interferon γ secretion after administration of Lactobacillus acidophilus," British journal of sports medicine 40: 351-354, 2006.
Clarke, S.L., et al., "Exercise and associated dietary extremes impact on gut microbial diversity," Gut 63: 1913-1920, 2014.

Cox, A.J., et al., "Oral administration of the probiotic Lactobacillus fermentum VRI-003 and mucosal immunity in endurance athletes," British Journal of Sports Medicine 44: 222-226, 2010 (Abstract Only).
Georges, J., et al., "The effects of probiotic supplementation on lean body mass, strength, and power, and health indicators in resistance trained males: a pilot study," Journal of the International Society of Sports Nutrition 11 (Suppl. 1): p. 38, 2014.
Gill, S.K., et al., "High-dose probiotic supplementation containing Lactobacillus casei for 7 days does not enhance salivary antimicrobial protein responses to exertional heat stress compared with placebo," International Journal of Sport Nutrition and Exercise Metabolism 26: 150-160, 2016.
Gleeson, M., et al., "Daily probiotic's (Lactobacillus casei Shirota) reduction of infection incidence in athletes," International Journal of Sport Nutrition and Exercise Metabolism 21: 55-64, 2011.
Hardin, B.J., et al., "TNF-alpha acts via TNFR1 and muscle-derived oxidants to depress myofibrillar force in murine skeletal muscle," J. Appl. Physiol. 104: 694-699, 2008.
Hayes, L.D., et al., "Exercise-induced responses in salivary testosterone, cortisol, and their ratios in men: a meta-analysis," Sports Medicine 45: 713-726, 2015.
Hong, H.A., et al., "The use of bacterial spore formers as probiotics," FEMS Microbiology Revs. 29: 813-835 (2005).
Ibrahim, N.S., et al., "The effects of combined probiotic ingestion and circuit training on muscular strength and power and cytokine responses in young males," Applied Physiology, Nutrition, and Metabolism (2018) 43: 180-186.
Keller, D., et al., "Bacillus coagulans GBI-30, 6086 increases plant protein digestion in a dynamic, computer-controlled in vitro model of the small intestine (TIM-1)," Beneficial microbes 8: 491-496, 2017.
Lamprecht, M., et al., "Probiotic supplementation affects markers of intestinal barrier, oxidation, and inflammation in trained men; a randomized, double-blinded, placebo-controlled trial," Journal of the International Society of Sports Nutrition 9: 45, 2012.
Lang, C.H., et al., "TNF-α impairs heart and skeletal muscle protein synthesis by altering translation initiation," American Journal of Physiology—Endocrinology and Metabolism 282: E336-E347, 2002.
Lee, E.C., et al., "Biomarkers in Sports and Exercise: Tracking Health, Performance, and Recovery in Athletes," Journal of Strength and Conditioning Research 31: 2920, 2017.

(Continued)

*Primary Examiner* — Brian Gangle
(74) *Attorney, Agent, or Firm* — Amin Wasserman Gurnani LLP; Jonathan J. Krit; George M. Carrera, Jr.

(57) ABSTRACT

Methods of using *Bacillus subtilis* probiotic supplementation to promote lower circulating TNF-α in resistance trained males are presented. Methods of administering *Bacillus subtilis* probiotic supplementation to an athletic population in conjunction with a sound nutrition and training regimen are presented herein. College athletes typically undergo periods of elevated stress both physically and mentally which may negatively affect recovery and adaptation. 12-weeks of probiotic supplementation resulted in attenuated circulating TNF-α concentrations in college athletes following offseason training.

12 Claims, No Drawings

(56)  References Cited

OTHER PUBLICATIONS

Lescheid, D.W., "Probiotics as regulators of inflammation: A review," Functional Foods in Health and Disease 4: 299-311, 2014.

Mach, N., et al., "Endurance exercise and gut microbiota: A review," Journal of Sport and Health Science 6: 179-197, 2017.

Mackinnon, L.T., et al., "Decreased secretory immunoglobulins following intense endurance exercise," Research in Sports Medicine: An International Journal 1: 209-218, 1989 (Abstract Only).

Mackinnon, L.T., et al., "Decreased salivary immunoglobulin A secretion rate after intense interval exercise in elite kayakers," European Journal of Applied Physiology and Occupational Physiology 67: 180-184, 1993.

Mackinnon, L.T., et al., "Decreased salivary immunoglobulins after intense interval exercise before and after training," Medicine and Science in Sports and Exercise 25: 678-683, 1993 (Abstract Only).

Main, L.C., et al., "Relationship between inflammatory cytokines and self-report measures of training overload," Research in Sports Medicine 18: 127-139, 2010.

Michalickova, D., et al., "Lactobacillus helveticus Lafti L10 supplementation reduces respiratory infection duration in a cohort of elite athletes: a randomized, double-blind, placebo-controlled trial," Applied Physiology, Nutrition, and Metabolism 41: 782-789, 2016.

Peake, J., et al., "Characterization of inflammatory responses to eccentric exercise in humans," Exercise Immunology Review 11: 64-85, 2005.

Petersen, A.M.W., et al., "The anti-inflammatory effect of exercise," Journal of Applied Physiology 98: 1154-1162, 2005.

Schipper, R.G., et al., "Saliva as research material: biochemical, physicochemical and practical aspects," Archives of Oral Biology 52: 1114-1135, 2007.

Schmidt, K., et al., "Prebiotic intake reduces the waking cortisol response and alters emotional bias in healthy volunteers," Psychopharmacology 232: 1793-1801, 2015.

Steerenberg, P.A., et al., "Salivary levels of immunoglobulin A in triathletes," European Journal of Oral Sciences 105: 305-309, 1997.

Tiollier, E., et al., "Effect of a probiotics supplementation on respiratory infections and immune and hormonal parameters during intense military training," Military Medicine 172: 1006-1011, 2007.

Toohey, J.C., et al., "Effects of probiotic (Bacillus subtilis) supplementation during offseason resistance training in female Division I athletes," The Journal of Strength and Conditioning Research, (2018, in press).

Toohey, J.C., et al., "Effects of probiotic (Bacillus subtilis) supplementation during offseason resistance training in female Division I athletes," The Journal of Strength and Conditioning Research, 34: 3173-3181, 2020 (Abstract Only).

Townsend Jr et al., "Effects of Probiotic (Bacillus subtilis DE111) Supplementation on Immune Function, Hormonal Status, and Physical Performance in Division I Baseball Players", Sports (Basel). Jul. 26, 20186;6(3):70.

Trochimiak, T., et al., "Effect of exercise on the level of immunoglobulin A in saliva," Biology of Sport 29: 255-261, 2012.

West, N.P., et al., "Lactobacillus fermentum (PCC®) supplementation and gastrointestinal and respiratory-tract illness symptoms: a randomised control trial in athletes," Nutrition Journal 10: 30, 2011.

BACILLUS SUBTILIS PROBIOTICS AND METHODS OF USE FOR IMPROVING IMMUNE FUNCTION, HORMONAL STATUS, AND PHYSICAL PERFORMANCE

This application is a Continuation-in-Part of U.S. application Ser. No. 16/593,469, filed on Oct. 4, 2019, which claims the benefit of U.S. Provisional Application No. 62/741,300 filed on Oct. 4, 2018. The disclosures of the prior applications are each incorporated by reference in their entireties for all purposes.

TECHNICAL FIELD

The present invention relates to methods of using *Bacillus subtilis* (DE111) probiotic supplementation to attenuate circulating markers of inflammation and catabolism, e.g. TNF-$\alpha$ concentrations, in athletes following offseason training and methods of administering *Bacillus subtilis* probiotic supplementation to an athletic population in conjunction with a sound nutrition and training regimen.

BACKGROUND

Athletes regularly engage in rigorous exercise training which leads to accumulating amounts of physical stress. While daily moderate intensity physical activity has been shown to have positive effects on the immune system (Petersen A M W and Pedersen B K. The anti-inflammatory effect of exercise. *Journal of applied physiology* 98: 1154-1162, 2005), prolonged periods of intense training and competition may lead to immune dysregulation (Gleeson M, McDonald W, Cripps A, Pyne D, Clancy R, and Fricker P. The effect on immunity of long-term intensive training in elite swimmers. *Clinical & Experimental Immunology* 102: 210-216, 1995; Mackinnon L T, Ginn E, and Seymour G J. Decreased salivary immunoglobulin A secretion rate after intense interval exercise in elite kayakers. *European journal of applied physiology and occupational physiology* 67: 180-184, 1993; Mackinnon L T and Jenkins D G. Decreased salivary immunoglobulins after intense interval exercise before and after training. *Medicine and science in sports and exercise* 25: 678-683, 1993). As a result of mucosal and systemic immune suppression, it is common for competitive athletes to become susceptible to infections, which may reduce the frequency and quality of physical training and athletic competition (Fahlman M M and Engels H-J. Mucosal IgA and URTI in American college football players: a year longitudinal study. *Medicine and science in sports and exercise* 37: 374-380, 2005). In addition to being vulnerable to infection, overly fatigued athletes are found to have altered levels of pro and anti-inflammatory cytokines in circulation (Gepner Y, Hoffman J R, Shemesh E, Stout J R, Church D D, Varanoske A N, Zelicha H, Shelef I, Chen Y, and Frankel H. Combined effect of *Bacillus coagulans* GBI-30, 6086 and HMB supplementation on muscle integrity and cytokine response during intense military training. *Journal of Applied Physiology* 123: 11-18, 2017; Hoffman J R, Gepner Y, Stout J R, Hoffman M W, Ben-Dov D, Funk S, Daimont I, Jajtner A R, Townsend J R, and Church D D. β-Hydroxy-β-methylbutyrate attenuates cytokine response during sustained military training. *Nutrition research* 36: 553-563, 2016). For instance, elevated circulating TNF-$\alpha$ in elite male rowers was significantly associated to depressed mood, sleep disturbances, and physical stress (Main L C, Dawson B, Heel K, Grove J R, Landers G J, and Goodman C. Relationship between inflammatory cytokines and self-report measures of training overload. *Research in Sports Medicine* 18: 127-139, 2010). Moreover, TNF-$\alpha$ acts to impair protein synthesis in skeletal muscle by decreasing mRNA translational efficiency (Lang C H, Frost R A, Nairn A C, MacLean D A, and Vary T C. TNF-$\alpha$ impairs heart and skeletal muscle protein synthesis by altering translation initiation. *American Journal of Physiology-Endocrinology and Metabolism* 282: E336-E347, 2002). This combination of factors may limit an athlete's ability to properly recover from acute training bouts and may ultimately impair training adaptations.

While athletes are often subjected to excessive levels of physical stress as a byproduct of training demands, other stressors are often overlooked. For instance, collegiate athletes regularly engage in periods of high physical stress accompanied with prolonged travel, academic rigor, and other physiological stressors. College athletes who are under a large amount of physical and academic stress have recently been shown to be more susceptible to sustaining injury during these times of increased strain (Mann J B, Bryant K R, Johnstone B, Ivey P A, and Sayers S P. Effect of physical and academic stress on illness and injury in division 1 college football players. *The Journal of Strength & Conditioning Research* 30: 20-25, 2016). To counter this, biomarker monitoring is gaining momentum in the athletic realm as a method to detect periods of excessive negative physiological stress (Lee E C, Fragala M S, Kavouras S A, Queen R M, Pryor J L, and Casa D J. Biomarkers in Sports and Exercise: Tracking Health, Performance, and Recovery in Athletes. *Journal of strength and conditioning research* 31: 2920, 2017). Furthermore, it has been suggested that utilizing an assembly of diverse biomarkers may provide the most effective strategy in evaluating intricate balance of anabolic and catabolic processes in athletes (MacKinnon LT. Overtraining effects on immunity and performance in athletes. *Immunology & Cell Biology* 78: 502-509, 2000; Smith L L. Cytokine hypothesis of overtraining: a physiological adaptation to excessive stress? *Medicine & Science in Sports & Exercise* 32: 317, 2000).

To attenuate the increasing levels of physiological strain associated with training, athletes often implement nutritional strategies to support immune health. Probiotic supplementation, for instance, is a strategy which is receiving considerable attention as a countermeasure for training-induced stressors (Pyne D B, West N P, Cox A J, and Cripps A W. Probiotics supplementation for athletes—clinical and physiological effects. *European journal of sport science* 15: 63-72, 2015). Probiotics are live organisms that when consumed, impose a wide array of beneficial physiological effects on humans, most notably promoting improved gut microbiota (Borchers A T, Selmi C, Meyers F J, Keen C L, and Gershwin M E. Probiotics and immunity. *Journal of gastroenterology* 44: 26-46, 2009). These microorganisms have been shown to exert immunomodulatory effects (Lescheid D W. Probiotics as regulators of inflammation: A review. *Functional foods in health and disease* 4: 299-311, 2014) by decreasing pro-inflammatory cytokines in circulation (Lamprecht M, Bogner S, Schippinger G, Steinbauer K, Fankhauser F, Hallstroem S, Schuetz B, and Greilberger J F. Probiotic supplementation affects markers of intestinal barrier, oxidation, and inflammation in trained men; a randomized, double-blinded, placebo-controlled trial. *Journal of the International Society of Sports Nutrition* 9: 45, 2012) and supporting mucosal defense (Gleeson M, Bishop N C, Oliveira M, and Tauler P. Daily probiotic's (*Lactobacillus casei* Shirota) reduction of infection incidence in athletes. *International journal of sport nutrition and exercise metabo-*

*lism* 21: 55-64, 2011; Michalickova D, Minic R, Dikic N, Andjelkovic M, Kostic-Vucicevic M, Stojmenovic T, Nikolic I, and Djordjevic B. *Lactobacillus helveticus* Lafti L10 supplementation reduces respiratory infection duration in a cohort of elite athletes: a randomized, double-blind, placebo-controlled trial. *Applied Physiology, Nutrition, and Metabolism* 41: 782-789, 2016). As probiotics have previously been shown to modulate pro- and anti-inflammatory cytokines in the body, it has been suggested that probiotics may support an athlete's general immune health (Pyne, et al., 2015). Additionally, intense physical training may cause damage to an athlete's gut barrier, resulting in endotoxin translocation, oxidative stress, and a low-grade pro-inflammatory cytokine response (Lamprecht, et al., 2012; Martarelli D, Verdenelli M C, Scuri S, Cocchioni M, Silvi S, Cecchini C, and Pompei P. Effect of a probiotic intake on oxidant and antioxidant parameters in plasma of athletes during intense exercise training. *Current microbiology* 62: 1689-1696, 2011; Pugh J N, Impey S G, Doran D A, Fleming S C, Morton J P, and Close G L. Acute high-intensity interval running increases markers of gastrointestinal damage and permeability but not gastrointestinal symptoms. *Applied Physiology, Nutrition, and Metabolism* 42: 941-947, 2017; Van Wijck K, Lenaerts K, Van Loon L J, Peters W H, Buurman W A, and Dejong C H. Exercise-induced splanchnic hypoperfusion results in gut dysfunction in healthy men. *PloS one* 6: e22366, 2011). In athletes, probiotics have been reported to reduce the number, duration, and severity of infections (Gleeson, et al., 2011; Cox A J, Pyne D B, Saunders P U, and Fricker P A. Oral administration of the probiotic *Lactobacillus fermentum* VRI-003 and mucosal immunity in endurance athletes. *British Journal of Sports Medicine* 44: 222-226, 2010; West N P, Pyne D B, Cripps A W, Hopkins W G, Eskesen D C, Jairath A, Christophersen C T, Conlon M A, and Fricker P A. *Lactobacillus fermentum* (PCC®) supplementation and gastrointestinal and respiratory-tract illness symptoms: a randomised control trial in athletes. *Nutrition Journal* 10: 30, 2011). Thus by improving resistance to infection, attenuating low-grade inflammation, and improving nutrient absorption, probiotic supplementation may be a practical strategy to support athlete health and adaptation (Pyne, et al., 2015; Coqueiro A Y, de Oliveira Garcia A B, Rogero M M, and Tirapegui J. Probiotic supplementation in sports and physical exercise: Does it present any ergogenic effect? *Nutrition and health* 23: 239-249, 2017).

While probiotic supplementation appears to have a generally positive effect on athlete immune function, its efficacy on improving exercise performance is less clear. In endurance athletes, a multi-strain probiotic significantly improved time until fatigue in males running at 80% of their ventilatory threshold (Shing C M, Peake J M, Lim C L, Briskey D, Walsh N P, Fortes M B, Ahuja K D, and Vitetta L. Effects of probiotics supplementation on gastrointestinal permeability, inflammation and exercise performance in the heat. *European journal of applied physiology* 114: 93-103, 2014) whereas others have reported no effect of probiotics on performance (Cox, et al., 2010; Michalickova, et al., 2016; West, et al., 2011). Regarding resistance exercise, Jäger, et al., found that co-ingestion of protein with a *Bacillus* strain probiotic attenuated range of motion decrements in recovery following an intense bout of resistance exercise possibly by improving nutrient absorption (Jager R, Purpura M, Stone J D, Turner S M, Anzalone A J, Eimerbrink M J, Pane M, Amoruso A, Rowlands D S, and Oliver J M. Probiotic *Streptococcus thermophilus* FP4 and *Bifidobacterium breve* BR03 supplementation attenuates performance and rangeof-motion decrements following muscle damaging exercise. *Nutrients* 8: 642, 2016; and also Keller D, Van Dinter R, Cash H, Farmer S, and Venema K. *Bacillus coagulans* GBI-30, 6086 increases plant protein digestion in a dynamic, computer-controlled in vitro model of the small intestine (TIM-1). *Beneficial microbes* 8: 491-496, 2017). Furthermore, 10-weeks of *Bacillus subtilis* supplementation in conjunction with adequate post-workout nutrition was shown to improve body composition in female collegiate athletes (Toohey, J C, Townsend J R, Johnson S B, Toy A M, Vantrease W C, Bender D, Crimi C C, Stowers K L, Ruiz M D, VanDusseldorp T A, Feito Y, Mangine G T, "The effects of probiotic (*Bacillus subtilis*) supplementation during off-season resistance training in female Division I athletes," *The Journal of Strength and Conditioning Research*, (2018, in press).

Despite recent interest, the effects of probiotic supplementation on training outcomes in resistance-trained individuals and on their performance is still unclear (Georges J, Lowery R P, Yaman G, Kerio C, Ormes J, McCleary S A, Sharp M, Shields K, Rauch J, and Silva J. The effects of probiotic supplementation on lean body mass, strength, and power, and health indicators in resistance trained males: a pilot study. *Journal of the International Society of Sports Nutrition* 11, 2014; Ibrahim N S, Muhamad A S, Ooi F K, Meor-Osman J, and Chen C K, "The effects of combined probiotic ingestion and circuit training on muscular strength and power and cytokine responses in young males," *Applied Physiology, Nutrition, and Metabolism* (2018) 43: 180-186).

SUMMARY OF THE INVENTION

In an embodiment, the present invention examines the effect of daily probiotic supplementation on strength, performance, body composition and biochemical markers in Division I male college athletes. The test results indicate that probiotic supplementation may provide additional benefits on strength, performance, and body composition following offseason training compared to placebo ("PL"). Furthermore, probiotic supplementation promotes lower circulating TNF-α in resistance trained males. These findings provide a method of administering probiotic supplementation in an athletic population in conjunction with a sound nutrition and training regimen.

In another embodiment, a method is described for improving physical performance in a human, comprising the steps of: (a) administering orally to the human a composition comprising *Bacillus subtilis* in a dose of from about $1 \cdot 10^8$ CFU per day to about $1 \cdot 10^{11}$ CFU per day; and (b) measuring TNF-α level in blood plasma of the human. The administering step can be performed for about 10-12 weeks.

In another embodiment, a method of reducing TNF-α in human serum is described, comprising the steps of: (a) administering orally to the human a composition comprising *Bacillus subtilis* in a dose of from about $1 \cdot 10^8$ CFU per day to about $1 \cdot 10^{11}$ CFU per day for about 12 weeks; and (b) submitting the human to a resistance training program throughout the 12 weeks. The resistance program may include workouts 2-3 times per week.

DETAILED DESCRIPTION

In its principal embodiment, a *Bacillus subtilis* (*B. subtilis*) containing composition is used for probiotic supplementation in a human subject. One useful *Bacillus subtilis*-containing composition is DE111® ("DE111") available from Deerland Enzymes, Inc. (Kennesaw, Georgia). DE111 is an isolated strain of *Bacillus subtilis* subspecies *inaquosorum* having accession number NRRL B-67989. The *Bacillus subtilis* subspecies *inaquosorum* (DE111) strain was deposited with the Agricultural Research Service Culture Collection (NRRL), an International Depositary Authority, 1815 N. University Street, Peoria, Illinois, 61604, United States) under the Budapest Treaty on the International Recognition of the Deposit of Microorganisms, on Sep. 28, 2020 and was accepted and found to be viable on Sep. 28, 2020, and assigned accession number NRRL B-67989. The DE111 strain is a biologically pure culture prepared by a proprietary process. The probiotic supplement can include 5 billion CFU *Bacillis subtilis*.

As described herein, DE111® may be used in an effective total daily dose from about $1\times10^8$ CFU to about $1\times10^{11}$ CFU. One preferred daily dose range is from about $1\times10^9$ CFU to about $1\times10^{10}$ CFU.

The *Bacillus subtilis* DE111 strain has certain properties, which, surprisingly, have been found to make the strain well-suited for use as a probiotic. Spores of *Bacillus subtilis* are viable under a wide temperature and pH range. Without being bound by any particular theory, it is thought that the ability of *Bacillus subtilis* DE111 to form spores that protect the microbes from harsh conditions until they enter an environment ripe for germination, such as the GI tract, makes *Bacillus* particularly well-suited for use as a probiotic.

In one aspect of the invention, compositions administered to patients in need thereof according to the methods of the present disclosure comprise mutants of *Bacillus subtilis* DE111 having all the identifying characteristics of *Bacillus subtilis* DE111. Such mutants may have DNA sequence identity to *Bacillus subtilis* DE111 of at least about 90%, at least about 91%, at least about 92%, at least about 93%, at least about 94%, at least about 95%, at least about 96%, at least about 97%, at least about 98%, or at least about 99%. In some embodiments, mutants are spontaneous mutants. The teen spontaneous mutant refers to mutants that arise from *Bacillus subtilis* DE111 without the intentional use of mutagens. Such spontaneous mutants may be obtained by classical methods, such as growing the *Bacillus subtilis* DE111 strain in the presence of a certain antibiotic to which the parent is susceptible, and testing any resistant mutants for improved biological activity or, in this application, ability to improve the body composition of an individual. Other methods for identifying spontaneous mutants will be known to those of ordinary skill in the art.

All references in this application to *Bacillus subtilis* DE111 or its mutants refer to bacteria that have been isolated from nature and are grown by humans, for example, in the laboratory or under industrial conditions.

*Bacillus subtilis* DE111 cells may be present in the compositions administered to patients in need thereof according to the methods of the present disclosure as spores (which are dormant), as vegetative cells (which are growing), as transition state cells (which are transitioning from growth phase to sporulation phase) or as a combination of all of these types of cells. In some embodiments, the composition comprises mainly spores. In other embodiments, the composition comprises spores and metabolites produced by the cells during fermentation before they sporulate, as described below.

Compositions administered to patients in need thereof according to the methods of the present disclosure can be obtained by culturing *Bacillus subtilis* DE111 or its mutants according to methods well known in the art. Conventional large-scale microbial culture processes include submerged fermentation, solid state fermentation, or liquid surface culture. Towards the end of fermentation, as nutrients are depleted, *Bacillus subtilis* DE111 cells begin the transition from growth phase to sporulation phase, such that the final product of fermentation is largely spores, metabolites, and residual fermentation medium. Sporulation is part of the natural life cycle of *Bacillus subtilis* DE111 and is generally initiated by the cell in response to nutrient limitation. Fermentation is configured to obtain high levels of colony forming units of *Bacillus subtilis* DE111 and to promote sporulation. The bacterial cells, spores, and metabolites in culture media resulting from fermentation may be used directly or concentrated by conventional industrial methods, such as centrifugation, tangential-flow filtration, depth filtration, and evaporation. In some embodiments, the concentrated fermentation broth is washed, for example, via a diafiltration process, to remove residual fermentation broth and metabolites.

The fermentation broth or broth concentrate can be dried with or without the addition of carriers using conventional drying processes or methods such as spray drying, freeze drying, tray drying, fluidized-bed drying, drum drying, or evaporation. The resulting dry products may be further processed, such as by milling or granulation, to achieve a specific particle size or physical format. Carriers, described below, may also be added post-drying.

In embodiments in which compositions formulated separately from food or drink are administered to patients in need thereof according to the methods of the present disclosure, the concentration on a weight by weight basis (w/w) of (i) *Bacillus subtilis* DE111 or its mutants, (ii) metabolites of *Bacillus subtilis* DE111 or its mutants, or (iii) combinations of cells and metabolites in the formulated composition may be about 0.5%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 25%, about 30%, about 35%, about 40%, about 45%, about 50%, about 55%, about 60%, about 65%, about 70%, about 75%, about 80%, about 85%, about 90%, or about 95%. In some embodiments of compositions administered to patients in need thereof according to the methods of the present disclosure, where the concentrated formulation broth has been washed and dried without heat, such as via freeze drying, the concentration of *Bacillus subtilis* DE111 or its mutants in the final composition may be from about 90% to about 100%.

In certain embodiments, compositions administered to individuals in need thereof according to the methods of the present disclosure are administered to improve strength, performance and body composition. An effective amount of a composition administered to an individual in need thereof according to the methods of the present disclosure is an amount effective to improve body composition in comparison to an individual who has not been administered the composition but otherwise has been administered the same diet as has an individual administered the composition according to methods of the present disclosure. In other embodiments, an effective amount of a composition administered to an individual in need thereof according to the methods of the present disclosure is an amount effective to reduce body fat percentage in comparison to an individual who has not been administered the composition but otherwise has been administered the same diet as has an individual administered the composition according to the methods of the present disclosure.

Thus, in line with the above, embodiments of the present disclosure are directed to methods of improving body composition, and/or reducing body fat percentage, by administering to an individual in need thereof a composition comprising *Bacillus subtilis* DE111, a mutant of *Bacillus subtilis* DE111, metabolites of *Bacillus subtilis* DE111 or its mutants, or combinations of *Bacillus subtilis* DE111 or a mutant and metabolites of *Bacillus subtilis* DE111 or its mutants.

Without wishing to be bound by any particular theory, it is thought that increases to beneficial bacteria may be caused by stimulating growth of such bacteria or simply by selectively decreasing pathogenic bacteria, thereby giving the beneficial bacteria more space to grow and to attach to the gut wall and/or more efficient access to nutrients and growth factors. In addition, or alternatively, beneficial bacteria may modify the virulence factors of pathogenic bacteria, thus decreasing the virulence of the pathogenic bacteria. Harmful, disease-causing bacteria that may be decreased by the methods of the present disclosure include *Clostridia* spp. (such as *perfringens* and *dificille*), *Listeria* spp. (such as *Moncytogenes, seeligeri,* and *welshimeri*), *Salmonella* spp. (such as *enterica, arizonae, typhirium, enteridis,* and *bonglori*), *E. coli, Enterococus* spp. (such as *faecalis* and *faecium*), *Camphylobacter, Aeromonas* spp., *Staphylococcus aureus, Shigella dysenteria,* and *Vibrio* spp. In some embodiments, harmful, disease-causing microorganisms may be reduced by about 0.5 log, about 1 log, about 2 log, about 3 log, about 4 log, or about 5 log.

In another aspect, compositions administered according to methods of the present disclosure comprising *Bacillus subtilis* DE111, its mutants, and/or metabolites of *Bacillus subtilis* DE111 and/or its mutants may further include or be administered with other probiotics, such as other bacterial spore formers. Examples of probiotics are provided in H. A. Hong, et al., *The use of bacterial spore formers as probiotics,* 29 FEMS MICROBIOLOGY REVS. 813 (2005), incorporated by reference herein in its entirety.

In yet another aspect, compositions administered according to methods of the present disclosure may include or be administered with (either at the same time or at different times) anti-diarrheal agents, anti-gas agents, dietary fibers, antibiotics, such as methotrexate, anti-inflammatory drugs, amino acids, electrolytes, vitamins, and minerals.

In embodiments in which the compositions administered according to methods of the present disclosure comprise *Bacillus subtilis* DE111 or its mutants, the bacteria should be administered in an amount that is effective to improve body composition and/or reduce body fat percentage. In embodiments in which the compositions are being administered to improve body composition and/or reduce body fat percentage, the compositions should be administered at effective total daily doses of from about $1 \cdot 10^3$ CFU *Bacillus subtilis* DE111 to about $1 \cdot 10^{15}$ CFU *Bacillus subtilis* DE111. In other embodiments in which the compositions are being administered to improve body composition and/or reduce body fat percentage, the compositions should be administered at effective total daily doses of from about $1 \cdot 10^4$ CFU *Bacillus subtilis* DE111 to about $1 \cdot 10^{14}$ CFU *Bacillus subtilis* DE111. In yet other embodiments in which the compositions are being administered to improve body composition and/or reduce body fat percentage, the compositions should be administered at effective total daily doses of from about $1 \cdot 10^5$ CFU *Bacillus subtilis* DE111 to about $1 \cdot 10^{13}$ CFU *Bacillus subtilis* DE111. In yet other embodiments in which the compositions are being administered to improve body composition and/or reduce body fat percentage, the compositions should be administered at effective total daily doses of from about $1 \cdot 10^6$ CFU *Bacillus subtilis* DE111 to about $1 \cdot 10^{12}$ CFU *Bacillus subtilis* DE111. In yet other embodiments in which the compositions are being administered to improve body composition and/or reduce body fat percentage, the compositions should be administered at effective total daily doses of from about $1 \cdot 10^8$ CFU *Bacillus subtilis* DE111 to about $1 \cdot 10^{11}$ CFU *Bacillus subtilis* DE11. In yet other embodiments, a preferred effective total daily dose range is from about $1 \cdot 10^9$ CFU *Bacillus subtilis* DE111 to about $1 \cdot 10^{10}$ CFU *Bacillus subtilis* DE111. In yet another embodiment, *Bacillus subtilis* DE111 can be provided in a daily dose of about $5 \cdot 10^9$ CFU for several weeks, up to a total of about 10-12 weeks.

In an embodiment, administration of a *Bacillus subtilis* DE111 dose at about 5 billion CFU per day statistically improved body composition and/or statistically reduced body fat percentage of an individual. In contrast, the testing group administered placebo composition did not generate similar improvements.

In certain embodiments, the compositions administered according to the methods of the present disclosure may also include one or more excipients, most preferably one or more nutraceutical or pharmaceutical excipients. Compositions containing one or more excipients and incorporating one or more probiotics can be prepared by procedures known in the art. Optionally, compositions can include one or more adjuvants, excipients, carriers, buffers, diluents, and/or other customary pharmaceutical auxiliaries. For example, probiotics can be formulated into tablets, capsules, powders, suspensions, solutions for oral administration, solutions for parenteral administration including intravenous, intradermal, intramuscular, and subcutaneous administration, and solutions for application onto patches for transdermal application with common and conventional barriers, binders, diluents, and excipients.

In certain embodiments, nutraceutical compositions administered according to the methods of the present disclosure may be administered in combination with a pharmaceutically acceptable carrier. In certain embodiments, the active ingredients in such formulations may comprise from about 1% by weight to about 99% by weight. In other embodiments, the active ingredients in such formulations may comprise from about 0.1% by weight to about 99.9% by weight. "Pharmaceutically acceptable carrier" means any carrier, diluent, or excipient that is compatible with the other ingredients of the formulation and not deleterious to the user. Useful excipients include, but are not limited to, microcrystalline cellulose, magnesium stearate, calcium stearate, any acceptable sugar (e.g., mannitol, xylitol), and the like, and for cosmetic use, an oil-base is preferred.

In another embodiment, the dose of DE111 can be provided in a daily dose of about $1 \times 10^9$ CFU for several weeks, up to a total of about 12 weeks.

One embodiment of the present invention relates to the effects of 12-week of daily probiotic supplementation on the immune and hormonal profile in college athletes during a period of increased academic and physical stress. Another embodiment of the present invention relates to the effects of daily probiotic supplementation on physical and performance adaptations in Division I collegiate baseball players following 12-weeks of offseason training.

TNF-α is a potent pro-inflammatory cytokine which is designed to serve an essential role in skeletal muscle remodeling. However, pronounced levels of TNF-α have been linked suppressed protein synthesis, disordered sleep, and impaired muscular performance. Probiotic supplementation having different bacterial strains from those disclosed herein reduced circulating TNF-α concentrations in endurance trained men (Lamprecht, et al., 2012) while West, et al., (2011) found that probiotic supplementation likely decreased the magnitude of TNF-α concentrations following acute VO₂max testing.

IL-10 is an anti-inflammatory cytokine, which is generally elevated post resistance exercise as a means to suppress inflammation and begin the adaptation process (Hirose L, Nosaka K, Newton M, Laveder A, Kano M, Peake J, and Suzuki K. Changes in inflammatory mediators following eccentric exercise of the elbow flexors. *Exerc Immunol Rev* 10: 20, 2004; Peake J, Nosaka K K, and Suzuki K. Characterization of inflammatory responses to eccentric exercise in humans. 2005). Ibrahim, et al., (2018) using different bacterial strains from the disclosed invention found a significant increase in IL-10 concentrations following 12 weeks of circuit training alone and probiotic supplementation alone while the combination of circuit training and probiotics trended towards a significant elevation post intervention.

Immunoglobulins are a heterogeneous group of antimicrobial proteins which appear as the immune system's first line of defense in the response to an antigen (Trochimiak T and Hübner-Woźniak E. Effect of exercise on the level of immunoglobulin A in saliva. *Biology of sport* 29: 255, 2012). IgA is the principal immunoglobulin involved in host defense and has been shown to be suppressed following intense acute (Mackinnon L T, Chick T W, Van As A, and Tomasi T B. Decreased secretory immunoglobulins following intense endurance exercise. *Research in Sports Medicine: An International Journal* 1: 209-218, 1989; Mackinnon L T, Ginn E, and Seymour G J. Decreased salivary immunoglobulin A secretion rate after intense interval exercise in elite kayakers. *European journal of applied physiology and occupational physiology* 67: 180-184, 1993; Steerenberg P A, Asperen I A, Amerongen A N, Biewenga J, Mol D, and Medema G. Salivary levels of immunoglobulin A in triathletes. *European journal of oral sciences* 105: 305-309, 1997) and chronic training (Gleeson, et al., 2011; Mackinnon L T and Jenkins D G. Decreased salivary immunoglobulins after intense interval exercise before and after training. *Medicine and science in sports and exercise* 25: 678-683, 1993). Contrary to reports in endurance athletes (Gleeson, et al., 2011) and military cadets (Tiollier E, Chennaoui M, Gomez-Merino D, Drogou C, Filaire E, and Guezennec C Y. Effect of a probiotics supplementation on respiratory infections and immune and hormonal parameters during intense military training. *Military medicine* 172: 1006-1011, 2007), a number of studies in endurance athletes found no differences in SIgA or SIgM between groups following probiotic interventions ranging from 4-12 weeks (Clancy R, Gleeson M, Cox A, Callister R, Dorrington M, D' este C, Pang G, Pyne D, Fricker P, and Henriksson A. Reversal in fatigued athletes of a defect in interferon γ secretion after administration of *Lactobacillus acidophilus*. *British journal of sports medicine* 40: 351-354, 2006; Cox, et al., 2010; West, et al., 2011). Additionally, another study found no differences in SIgA protein concentration or secretion rate in 24 male and 6 female professional athletes of various sports (Michalickova, et al., 2016).

Testosterone and cortisol represent a hormonal parameters which provide a snapshot of the current anabolic status of an athlete (Lee, et al., 2017). Traditionally, these two endocrine biomarkers are utilized in male athletes to identify and prevent overtraining (Hayes L D, Grace F M, Baker J S, and Sculthorpe N. Exercise-induced responses in salivary testosterone, cortisol, and their ratios in men: a meta-analysis. *Sports Medicine* 45: 713-726, 2015). Previous work found no effect of probiotics on cortisol concentrations during a period of intense military training (Tiollier, et al., 2007). However, one study in a non-athletic population reported lower cortisol responses in participants who received a prebiotic (soluble fiber compounds which enhance the growth of gut microbiota) supplement daily for 3 weeks (Schmidt K, Cowen P J, Harmer C J, Tzortzis G, Errington S, and Burnet P W. Prebiotic intake reduces the waking cortisol response and alters emotional bias in healthy volunteers. *Psychopharmacology* 232: 1793-1801, 2015).

Zonulin is a protein, which plays a central role in modulating intercellular tight junctions in the intestinal endothelium. Of late, this protein has been proposed as a novel circulating marker of intestinal permeability. Previous work found that 14 weeks of probiotic supplementation resulted in significantly decreased levels of fecal zonulin, indicating an improvement in intestinal barrier integrity (Lamprecht, et al., 2012). Some investigations have observed compromised gut permeability in response to an acute exercise stress in trained participants following endurance and interval training (Mach N and Fuster-Botella D. Endurance exercise and gut microbiota: A review. *Journal of sport and health science* 6: 179-197, 2017; Pugh, et al., 2017). Clarke et al., (Clarke S F, Murphy E F, O'sullivan O, Lucey A J, Humphreys M, Hogan A, Hayes P, O'reilly M, Jeffery I B, and Wood-Martin R. Exercise and associated dietary extremes impact on gut microbial diversity. *Gut*: gutjnl-2013-306541, 2014) found that trained athletes possess a healthier, more diverse gut microbiota.

It has been proposed probiotic supplementation may improve gastrointestinal function resulting in increased absorption of dietary protein (Keller D, Van Dinter R, Cash H, Farmer S, and Venema K. *Bacillus coagulans* GBI-30, 6086 increases plant protein digestion in a dynamic, computer-controlled in vitro model of the small intestine (TIM-1). *Beneficial microbes* 8: 491-496, 2017), which may contribute to enhanced adaptations over the course of a training intervention. In a mouse model, 6-weeks of *Lactobacillus plantarum* produced augmented strength, muscle mass, and type I muscle fiber number while improving endurance swimming performance (Chen Y-M, Wei L, Chiu Y-S, Hsu Y-J, Tsai T-Y, Wang M-F, and Huang C-C. *Lactobacillus plantarum* TWK10 supplementation improves exercise performance and increases muscle mass in mice. *Nutrients* 8: 205, 2016).

To date, only two studies have investigated the effect of probiotic administration on resistance training adaptations. The first investigation (Ibrahim, et al., 2018) found no ergogenic benefit of a probiotic supplement on muscular strength and power following 12 weeks of circuit-resistance training which is in concert with previous work in endurance athletes reporting no effect of probiotics on performance (Cox, et al., 2010; Gill S K, Teixeira A M, Rosado F, Cox M, and Costa R J S. High-dose probiotic supplementation containing *Lactobacillus casei* for 7 days does not enhance salivary antimicrobial protein responses to exertional heat stress compared with placebo. *International journal of sport nutrition and exercise metabolism* 26: 150-160, 2016; Michalickova, et al., 2016; West, et al., 2011). The second study found no preferential benefit of daily *Bacillus subtilis* (5 billion CFU) supplementation on measures of physical performance following 10-weeks of offseason training in female Division I volleyball and soccer athletes (Toohey, et al., 2018). However, Toohey, et al. (2018) did observe significant improvements in body compositions which mimicked those seen in non-athletic populations.

The methods described above may be further understood in connection with the following Examples. In addition, the following non-limiting examples are provided to illustrate the invention. However, the person skilled in the art will appreciate that it may be necessary to vary the procedures for any given embodiment of the invention, e.g., vary the order or steps.

Example 1. Methods and Study Protocols

Methods

Twenty-five Division I male baseball athletes ($20.1\pm1.5$y, $85.5\pm10.5$ kg, $184.7\pm6.3$ cm) participated in this double blind, placebo-controlled, randomized study. Participants were randomly assigned to a probiotic (PRO; n=13) or placebo (PL; n=12) group. Following an explanation of all procedures, risks, and benefits, each participant provided their written informed consent prior to participation in this study. The research protocol was approved by the Institutional Review Board of the Lipscomb University prior to participant enrollment. Exclusion criteria included the use of probiotic supplementation, ergogenic aids, or suffering from any medical, muscular, or metabolic contraindications.

Study Protocol

Participants reported to the Human Performance Lab (HPL) on two separate occasions at the beginning and end of the 12-week training intervention following a 10-hour overnight fast. Additionally, athletes were instructed to report to the lab hydrated while abstaining from caffeine, alcohol, and vigorous exercise for at least 24 h prior to both laboratory testing sessions. During these visits the participants were tested for body composition, muscle thickness, and provided biological samples. Furthermore, athletes reported to their strength and conditioning coordinator on two separate occasions pre and post training, to measure one repetition maximum ("1RM") for squat and deadlift along with testing pro-agility, 10-yd sprint, and standing long jump. Pre-training all 1RM sessions began at the beginning of the fall semester the first week of classes. Post-training, 1RM and performance testing occurred the week prior to final examinations. Since the aim was to investigate biomarkers of fatigue and immune function during a stressful period, we chose to conduct our post-training biochemical sample collection during final examination week (Mann, et al., 2016). Additionally, as winter months have been shown to produce additional challenges to the immune system (West, et al., 2011), our post-testing biochemical sampling occurred in a winter month as well (December).

Supplementation Protocol

Both the PRO and PL groups completed daily supplementation for 12 weeks. The PRO supplement consisted of 1 billion colony forming units (CFU) *Bacillis subtilis*, (DE111®, Deerland Enzymes, Kennesaw, Georgia, USA). On training days, supplementation occurred immediately post-workout with a protein and carbohydrate recovery drink (27 g protein, 36 g carbohydrates, 2 g fat) in the presence of a study investigator. On weekend or non-training days, athletes were provided their respective supplements in individual bags and were required to consume their supplement with a normal meal and return the used supplement bags to establish compliance.

Nutritional Analysis

During the training and supplement intervention participants were asked to complete a three-day food log (two weekdays, one weekend day) on weeks one, nine, and 12. Dietary recalls were used to provide an estimate of total kilocalorie intake (kcal) and macronutrient distributions (carbohydrate, protein, and fat) of the athlete's typical weekly diet. All dietary analysis was completed using the MyFitnessPal application (Under Armour Inc., Baltimore, Maryland, USA), which contains a large, detailed US-branded food database.

Statistical Analysis

Prior to hypothesis testing, the Shapiro-Wilk test was used to evaluate the assumption of normality for dependent variables. Non-normally distributed data were transformed using the natural log. To identify differences between the experimental conditions on changes in muscle size and strength, an ANCOVA was performed on all measures collected at POST. Associated values collected at PRE were used as the covariate to eliminate the possible influence of initial score variances on the outcomes. Following any significant F-ratio, a paired-samples t-test was used to determine if significant difference existed between measures collected prior to and immediately following 12 weeks of training. Group differences were further assessed via effect sizes ($\eta^2$p; partial eta squared). Effect sizes were interpreted as small (0.01-0.059), medium (0.06-0.139), or large (>0.14) as previously recommended (Green S, Salkind N, and Akey T. Methods for controlling type I error across multiple hypothesis tests. *Using SPSS for Windows: Analysing and Understanding Data:* 395-396, 2000). An alpha level was set at p≤0.05, and all analyses were performed using SPSS version 24.0 (SPSS, Inc., Chicago, Illinois).

Offseason Training

All athletes completed the same triphasic undulating periodized resistance training program for 12 weeks (2-3 days·week$^{-1}$) (Table 1). Triphasic training is a common periodized resistance training program designed to allow an athlete to eccentrically and isometrically absorb energy before applying it in a dynamic movement (Dietz C and Peterson B. *Triphasic training: A systematic approach to elite speed and explosive strength performance.* Bye Dietz Sport Enterprise, 2012). This program consists of three mesocyles (3-4 weeks) in which athletes emphasize a particular phase of movement (eccentric, isometric, concentric) while performing their core lifts. In addition to strength training, the athletes participated in team conditioning, agility, jumping, and sprint work (2-3 sessions·week$^{-1}$). These workouts consisted of approximately 30-40 minutes of sport-specific skill development and conditioning-related work. All training sessions were performed under the supervision of a certified strength and conditioning specialist as well as a certified athletic trainer.

TABLE 1

| 12-week Offseason Resistance Training Program | | | | | |
|---|---|---|---|---|---|
| Phase 1-Eccentric Weeks 1-4 | | | | | |
| Day 1 | Sets × Reps | Day 2 | Sets × Reps | Day 3 | Sets × Reps |
| Squat | 4 × 8-5 | Dead Lift | 4 × 8-5 | Hang Clean | 4 × 8-5 |
| Box jump | w/;03-;05 ECC | Single Hops | 4 × :08 seconds | Single Leg Box Jumps | 4 × 5 |
| | 4 × 4 | Single Leg Box | 4 × 5 | Inverted Row | 4 × 10 |
| Mobility | 3 × 10 | Squats | | Single Arm Dumbbell | 4 × 8-6 |
| Bench Press | 4 × 8-5 | Scap Angels | 3 × 10 | Bench | |
| 3 Point Row | w/;03-;05 ECC | Dumbbell Incline | 4 × 8-4 | Exercise Ball Core | 4 × 6 |
| | 4 × 8 | Press | | Sled Push | 4 × 1 |
| GHD Falls | w/;03-;05 ECC | Banded Swimmers | 4 × 10 | Banded Hip Flexer Pull | 4 × 10 |
| | 3 × 8 | Row | | | |
| | | Banded Face Pull | 4 × 10 | | |
| | | 6 Pack Scaps YTA | 3 × 6:03 ECC | | |
| Circuit 1 50:10 × 3 | Circuit 2 | Circuit 1 | Circuit 2 | Circuit 1 | Circuit 2 |
| Int/Ext Shoulder Rotation | Split Squat | Airex Floor Touches | Keiser Resisted Lunge | Band Pull-Aparts | Box Step-ups |
| Plank | TGU | Banded Hip Lifts | Banded × Walks | Keiser SL Twist | Ab Wheel |
| HK Chops | Pullup | Shoulder Raises | Side Plank Row | Kettle Bell Lunge | Med Ball Slams |
| Phase 2-Isometric Weeks 5-8 | | | | | |
| Day 1 | Sets × Reps | Day 2 | Sets × Reps | | |
| Hang Clean | 4 × 6-4 | Dead Lifts | 4 × 6-4 | | |
| Mobility | 3 × 5 | SL Hexagon Hops | 4 × :08 | | |
| | 4 × 6-4 | W/Y Negatives | 3 × 8 | | |
| Squat | w/;03-;05 ISO | SL Pistol Squat | 4 × 5 | | |
| Lateral Box Jump | 4 × 4 | Bench Press | 4 × 6-4 w/:03 ISO | | |
| DB Incline Bench Press | 4 × 6-4 | Battle Rope | 3 × :30 | | |
| Bear Row | w/;03 ISO | Variations | | | |
| | 4 × 8-6 | Black Burns | 3 × 5 | | |
| Sled Push | w/;03 ISO | SL RDL Reaches | 3 × 8 | | |
| | 3 × 1 | TRX Archor Row | 3 × 8 | | |
| Lateral Lunge | 3 × 8 | Landmine Rotation | 3 × 8 | | |
| Farmers Carry | 3 × 3 | and Press | | | |
| Pull-ups | 2 × 8, 1 × 6 | Med Ball Fielding | 3 × 10 | | |
| Standing Keiser Twists | w/;03 ISO | Drill | | | |
| | 3 × 10 | Excercise Ball Knee | 3 × 10 | | |
| | | Drives | | | |
| Phase 3-Concentric Weeks 9-12 | | | | | |
| Day 1 | Sets × Reps | Day 2 | Sets × Reps | Day 3 | Sets × Reps |
| Squat | 4 × 4-2 | Dead Lift | 4 × 4-2 | Hang Clean | 4 × 4-2 |
| Box Jump | 4 × 4 | lateral Bound | 4 × 6 | Dead Bugs | 4 × 5 |
| Mobility | 3 × 5 | Inverted Row | 3 × 8 | Cross-Over ATYT | 3 × 15 |
| Incline Bench | 4 × 4-3 | Bench Press | 4 × 4-3 | Mobility | 3 × 10 |
| 3 Point Row | 4 × 5-3 | Med Ball Chest Pass | 4 × 5 | Single Arm Bench | 4 × 4-3 |
| Hip Lift | 4 × 6 | BlackBurns | 4 × 5 | 6 Pack Scaps | 4 × 6 |
| Battle Rope Variations | 3 × :30 | Single Leg Squat | 4 × 5 | Lateral Sled Pull | 3 × 1 |
| Inline Board Lunge | 3 × 5 | Side Plank Row | 3 × 8 | Keiser Single Arm | 3 × 8 |
| Pull-up | 3 × 8 | Band Pull-Aparts | 3 × 10 | Single Leg Row | |
| Keiser Low Row | 3 × 8 | Val Slide Lateral | 3 × 8 | Med Ball Slams | 3 × 10 |
| Supine Bridge w/ Cross | 3 × 10 | Lunge | | Towel Pull-ups | 3 × 8 |
| Body Med Ball Throw | | Landmine Touches | 3 × 10 | Vertimax Pull Over | 3 × 10 |
| | | Prone Hip Openers | 3 × 10 | | |

Results

No significant differences were observed between groups for compliance, with all athletes achieving ≥92% with an average compliance of 98.8% across groups. No significant differences in average daily caloric intake were observed between PRO (2404±494.3 kcals) and PL (2369±616.3 kcals) groups. In addition, no significant differences were seen between groups in carbohydrate (PRO: 262.2±52.3 g vs. PL: 251.4±62.6 g), protein (PRO: 122.3±33.3 g vs. PL: 128.0±40.1 g) and fat (PRO: 91.3±28.7 g vs. PL: 86.5±24.1 g) intakes. Furthermore, both PRO and PL supplements were well tolerated, and no adverse side effects were reported.

Example 2. Body Composition, Muscle Density, Strength and Physical Performance

Body Composition

Air Displacement Plethysmography

Body density was estimated using air displacement plethysmography using the BODPOD® (COSMED, Rome, Italy). Prior to each test, the BODPOD was calibrated according to the manufacturer's instructions using a two-point calibration. Prior to testing, athletes were instructed to wear tight fitting compression shorts and a swimming cap, as well as to remove all metal, including jewelry and watches. Body mass was measured to the nearest 0.01 kg using the system's calibrated scale. All athletes were instructed to sit in the chamber, breath normally, and to minimize any movement. A minimum of two trials were performed. If measurements were not within 150 ml of each other, a third trial was conducted. Thoracic gas volume was estimated using the BODPOD software, which uses standard prediction equations and has demonstrated no difference compared to measured lung volumes (McCrory M A, Molé P A, Gomez T D, Dewey K G, and Bernauer E M. Body composition by air-displacement plethysmography by using predicted and measured thoracic gas volumes. *Journal of Applied Physiology* 84: 1475-1479, 1998).

Bioelectrical Impedance Analysis

Total body water (TBW) was determined using multi-frequency bioelectrical impedance analysis (BIA) using the InBody® 570 Body Composition Analyzer device (Biospace, Inc., Seoul, Korea). Body composition from BIA is obtained from the measures of resistance and reactance when an electrical current travels throughout the body. Prior to each assessment the participants' hands and feet were thoroughly cleaned with InBody® provided tissues. Age, height, and sex were manually entered, while a scale positioned within the device assessed body mass. The participant was then instructed from the software to stand fully erect on the measurement electrodes situated on the platform and to hold hand electrodes, with arms extended, without touching the sides of their body. Participants were asked to refrain from moving or talking until the assessment was completed. It has previously been shown that BIA is a valid measurement tool for determining TBW when compared to a deuterium oxide technique (Anderson L J, Erceg D N, and Schroeder E T. Utility of multi-frequency bioelectrical impedance compared to deuterium dilution for assessment of total body water. *Nutrition & dietetics* 72: 183-189, 2015).

Three-Compartment Model (3C-W)

The criterion percent body fat (% BF) was estimated using the three compartment-water (3C-W) model described by Sin (Siri W E. The gross composition of the body. *Adv Biol Med Phys* 4: 513, 1956). The equation includes measurements of body density (from the BODPOD), TBW (from the BIA), and body mass (BM). The equation for % BF is listed below:

$$\% \ BF=[(2.118/\text{Body density})-(0.78 \times \text{TBW (L)/BM (kg)})-1.354] \times 100 \qquad \text{Equation (1)}$$

Muscle Ultrasonography

Non-invasive measurements of muscle thickness (MT) were collected using B-mode ultrasound imaging with a 12 MHz linear probe (General Electric LOGIQ P5, Wauwatosa, Wisconsin). Measurements for the rectus femoris (RF) were taken at 50% of the distance from the anterior, inferior suprailliac spine to the most proximal point of the patella (Jajtner A R, Hoffman J R, Scanlon T C, Wells A J, Townsend J R, Beyer K S, Mangine G T, McCormack W P, Bohner J D, and Fragala M S. Performance and muscle architecture comparisons between starters and nonstarters in National Collegiate Athletic Association Division I women's soccer. *The Journal of Strength & Conditioning Research* 27: 2355-2365, 2013). Vastus lateralis (VL) measurements were taken in the same fashion as previously stated; however, the sampling location is determined by 50% the straight-line distance between the greater trochanter and the lateral epicondyle of the femur (Abe T, Fukashiro S, Harada Y, and Kawamoto K. Relationship between sprint performance and muscle fascicle length in female sprinters.

*Journal of physiological anthropology and applied human science* 20: 141-147, 2001). Prior to image collection, participants laid supine for 5 minutes and the probe was coated with a water-based conduction gel (Arroyo E, Stout J R, Beyer K S, Church D D, Varanoske A N, Fukuda D H, and Hoffman J R. Effects of supine rest duration on ultrasound measures of the vastus lateralis. *Clinical physiology and functional imaging* 38: 155-157, 2018). For measurements of MT, the probe was oriented longitudinally in the sagittal plane parallel to the muscle tissue without depressing the skin. Once images were collected, analysis was completed using Image J software (version 1.45s; National Institutes of Health, Bethesda, Maryland, USA). MT was determined from the still image as the distance between the inferior border of the superficial apo neurosis and the superior border of the deep aponeurosis. Intraclass correlation coefficients ($ICC_{3,k}$) and standard error of measurements (SEM) for the ultrasound technician were calculated for the RF MT ($ICC_{3,k}$=0.99, $SEM_{3,k}$=0.07, MD=0.19 cm) and VL MT ($ICC_{3,k}$=0.99, $SEM_{3,k}$=0.01, MD=0.03 cm) from analysis of 10 individuals separated by 24 hours.

Dynamic Strength Testing

One-repetition maximum (1RM) strength was assessed in squat and dead lift exercises. All 1RM testing was performed using methods previously described (Hoffman, J. *Norms for Fitness, Performance, and Health* (Human Kinetics: Champaign, Illinois, 2006.) Prior to testing, each athlete completed a general warm-up led by the strength and conditioning coach, which included jogging and a dynamic warm-up. Each athlete performed two warm-up sets using a resistance of approximately 40-60% and 60-80% of her perceived maximum, respectively. For each exercise 3-4 subsequent trials were performed to determine the 1-RM. A 3-5 min rest period was provided between each trial. Trials not meeting the range of motion criteria for each exercise or where proper technique was compromised were discarded.

Performance Testing

Ten-Yard Sprint

The athletes then completed a standardized general and dynamic warm-up that was consistent with their normal training habits and led by each teams' strength and conditioning coach. A pair of cones and tape affixed to the floor were positioned to denote the "starting line". The athletes were instructed to take their preferred starting stance at the starting line and to begin each maximal trial at their ready. The best of three trials was recorded and used for analysis.

Pro-Agility Test

For the pro-agility test, three cones were placed parallel, five meters apart. The athletes set up for the test in a straddle position facing the middle cone. On their ready, the athletes were instructed to pivot to their right and accelerate as quickly as possible to a cone 5 m away and then upon touching the first cone, pivot again to their left and sprint the 10 m distance to the furthest cone. Upon touching this cone, the athletes once again pivoted to the right to return to the middle cone as quickly as possible. During each change in direction, the athletes were asked to touch the ground next to the cone. Trials where the athlete failed to touch the ground were discarded. Athletes were allowed three attempts and the fastest time measured in seconds was recorded.

Standing Long Jump

Standing long jump performance was assessed using a pre-marked (±0.5 in) commercial mat (Sportime, LLC, Norcross, Georgia, USA). Prior to the test, each athlete stood with both feet placed in the marked "starting area" on the mat. Athletes were instructed to perform a maximal horizontal long jump. Standing long jump distance was determined by furthest distance reached following 3 maximal countermovement jump attempts performed from a standing position with feet shoulder width apart.

Results

Changes in strength, performance and body composition are presented in Table 2. There were no group differences observed between PRO and PL for any measure of strength, performance or body composition. Collectively, significant improvements (p<0.001) were observed in squat 1RM, deadlift 1RM, pro-agility, and standing long jump as a result of 12-weeks of offseason training while no improvement (p=0.312) in 10-yard sprint time was found. Additionally, both groups experienced significantly increased (p<0.001) RF and VL muscle thickness following training while no improvements were seen following Body Fat % (p=0.332).

While no differences in training outcomes were observed, probiotic supplementation still may foster a more favorable physiological state for recovery and adaptation.

In the current study, we observed no differences in any measure of physical performance between groups. Additionally, we found no preferential effects of probiotic supplementation on muscle thickness and body composition.

*Sports medicine* 26: 17-27, 1998). After collection, the sample tube was centrifuged at 3000 g for 15 min to remove cellular debris and which can negatively impact the accuracy of analysis (Schipper R G, Silletti E, and Vingerhoeds M H. Saliva as research material: biochemical, physicochemical and practical aspects. *Archives of oral biology* 52: 1114-1135, 2007). The supernatant was then aliquoted and stored frozen at −80° C. for later analysis.

Biochemical Analyses of Saliva Samples

Duplicate saliva samples were analyzed for secretory IgA and IgM concentrations using enzyme-linked immunosorbent assay (ELISA) kits (IgA: Salimetrics, State College, Pennsylvania, USA; IgM: Abcam, Toronto, Ontario, Canada). The intra-assay coefficient of variation for saliva IgA was 3.31% and 7.54% for IgM. The IgA and IgM secretion rate was then calculated by multiplying the concentration by the saliva flow rate.

Blood Sampling

These blood samples were obtained using a single-use disposable needle with the athlete in a supine position for at least 15 minutes before sampling. All blood samples were collected into two Vacutainer® tubes, one containing no anticlotting agent (6 mL) and the second containing

TABLE 2

Strength, Performance, and Body Composition Changes Following 12-weeks of Offseason Training

| Variable | | PRE | Covariate | POST | F | p | $\eta^2$ | 95% Confidence Interval Lower | Upper |
|---|---|---|---|---|---|---|---|---|---|
| Squat | PRO | 116.8 ± 17.1 | 124.9 | 141.8 ± 11.2 | .459 | .505 | .020 | 139.2 | 159.4 |
| 1RM (kg) | PL | 133.0 ± 32.0 | | 162.2 ± 40.0 | | | | 143.6 | 164.7 |
| Deadlift | PRO | 139.9 ± 12.2 | 151.3 | 169.4 ± 21.0 | .375 | .547 | .019 | 172.2 | 188.9 |
| 1RM (kg) | PL | 162.8 ± 40.5 | | 188.0 ± 39.1 | | | | 168.7 | 185.2 |
| Standing Long | PRO | 2.46 ± 0.17 | 2.50 | 2.55 ± 0.21 | .046 | .833 | .003 | 2.53 | 2.64 |
| Jump (m) | PL | 2.54 ± 0.28 | | 2.64 ± 0.19 | | | | 2.54 | 2.66 |
| Pro- | PRO | 4.62 ± 0.17 | 4.60 | 4.49 ± 0.22 | 1.152 | .300 | .071 | 4.41 | 4.55 |
| Agility (sec) | PL | 4.58 ± 0.20 | | 4.50 ± 0.23 | | | | 4.46 | 4.60 |
| 10 yd | PRO | 1.99 ± 0.86 | 1.86 | 1.69 ± 0.12 | .852 | .371 | .054 | 1.63 | 1.77 |
| Sprint (sec) | PL | 1.70 ± 0.11 | | 1.66 ± 0.09 | | | | 1.57 | 1.73 |
| Body Fat (%) | PRO | 14.7 ± 5.6 | 14.3 | 14.9 ± 4.8 | 2.119 | .161 | .096 | 13.7 | 15.7 |
| | PL | 14.0 ± 4.9 | | 13.4 ± 4.8 | | | | 12.9 | 14.6 |
| RF Muscle | PRO | 2.39 ± 0.44 | 2.44 | 2.51 ± 0.47 | .166 | .687 | .008 | 2.49 | 2.64 |
| Thickness (cm) | PL | 2.50 ± 0.28 | | 2.60 ± 0.29 | | | | 2.46 | 2.62 |
| VL Muscle | PRO | 1.73 ± 0.23 | 1.79 | 1.78 ± 0.23 | .513 | .481 | .023 | 1.81 | 1.89 |
| Thickness (cm) | PL | 1.86 ± 0.33 | | 1.93 ± 0.33 | | | | 1.83 | 1.91 |

Data presented as mean ± SD.

Example 3. Biomarker Level in Saliva and in Blood

Saliva Sampling

Saliva and blood samples were obtained at two time points throughout the study (PRE, POST). All biochemical samples at POST were taken at the same time of day as PRE to avoid potential confounding influence of diurnal variations. Prior to saliva sampling, all athletes rested in a seated position for 5 minutes. With an initial swallow to empty the mouth, unstimulated whole saliva was collected by expectoration into a pre-weighed vial for with eyes open, head tilted slightly forward and making minimal orofacial movement. Study personnel then documented the saliva collection duration and weight of the sample. Saliva flow rate (mL/min) was determined by weighing with saliva density assumed to be 1.0 g/mL (Chicharro J L, Lucía A, Pérez M, Vaquero A F, and Ureña R. Saliva composition and exercise.

$K_2EDTA$ (6 mL). The blood in the first tube was centrifuged immediately at 3000 g for 15 min while the second tube was allowed to clot at room temperature for 30 min and subsequently centrifuged at 3000 g for 15 min. The resulting plasma and serum were placed into separately labeled microcentrifuge tubes and frozen at −80° C. for later analysis.

Biochemical Analyses of Blood Samples

Circulating plasma concentrations of TNF-α and serum concentrations of IL-10, zonulin, testosterone, and cortisol were assayed via commercially available ELISA kits (ALPCO, Salem, New Hampshire, USA). To limit interassay variability, all samples for a particular assay were thawed once, and analyzed by the same technician using a FLUOstar Omega spectrophotometer (BMGLabtech, Ortenberg, Germany). All samples were analyzed in duplicate with a mean coefficient of variation of 4.05% for TNF-α, 7.45% for IL-10, 4.10% for zonulin, 4.89% for testosterone, and 3.48% for cortisol.

Results

Changes in Biochemical Markers are Presented in Table 3.

TABLE 3

Changes in Biochemical Markers Following 12-weeks of Offseason Training

| Variable | | PRE | Covariate | POST | F | p | $\eta^2$ | 95% Confidence Interval Lower | Upper |
|---|---|---|---|---|---|---|---|---|---|
| TNF-α | PRO | 2.32 ± 0.93 | 2.37 | 2.07 ± 0.76 | 5.857 | .024* | .210 | 1.69 | 2.49 |
| (pg/mL) | PL | 2.42 ± 1.49 | | 2.78 ± 0.95 | | | | 2.35 | 3.18 |
| LN IL-10 | PRO | 2.79 ± 0.97 | 2.95 | 2.89 ± 1.08 | .032 | .860 | .001 | 2.89 | 3.22 |
| (pg/mL) | PL | 3.12 ± 0.88 | | 3.27 ± 1.02 | | | | 2.91 | 3.25 |
| Zonulin | PRO | 10.59 ± 2.11 | 10.14 | 10.78 ± 2.23 | .010 | .921 | <0.001 | 9.68 | 11.04 |
| (ng/mL) | PL | 9.67 ± 4.32 | | 9.86 ± 4.27 | | | | 9.60 | 11.02 |
| Testosterone | PRO | 15.3 ± 6.59 | 15.7 | 15.8 ± 6.50 | 1.89 | .183 | 0.79 | 14.8 | 17.4 |
| (nmol/L) | PL | 16.2 ± 4.56 | | 17.8 ± 4.46 | | | | 16.0 | 18.8 |
| Cortisol | PRO | 656.3 ± 237.7 | 662.8 | 579.4 ± 183.2 | 3.411 | .078 | .134 | 488.9 | 678.0 |
| (nmol/L) | PL | 669.9 ± 224.1 | | 709.5 ± 247.4 | | | | 606.6 | 803.5 |
| T/C Ratio | PRO | .024 ± .009 | .025 | .030 ± .013 | .464 | .503 | .021 | .024 | .036 |
| | PL | .025 ± .008 | | .027 ± .009 | | | | .020 | .033 |
| Total WBC | PRO | 5.97 ± 1.50 | 5.84 | 7.08 ± 1.85 | .235 | .632 | .011 | 5.95 | 8.21 |
| (×10⁹/L) | PL | 5.71 ± 1.31 | | 7.46 ± 2.00 | | | | 6.28 | 8.64 |
| SIgA Secretion | PRO | 105.2 ± 56.4 | 123.1 | 176.6 ± 86.5 | 1.585 | .222 | .070 | 138.6 | 236.7 |
| Rate (µg/min) | PL | 141.1 ± 97.2 | | 156.1 ± 98.3 | | | | 96.0 | 194.1 |
| LN SIgM | PRO | 8.11 ± 1.45 | 8.07 | 8.84 ± 1.07 | .452 | .509 | .021 | 8.32 | 9.30 |
| Secretion Rate (µg/min) | PL | 8.02 ± 1.40 | | 8.55 ± 1.50 | | | | 8.10 | 9.07 |

Data presented as mean ± SD.
LN = natural log transformation.
*significantly different from PL TNF-α concentrations were significantly (F=5.859, p=0.024 $\eta^2$=0.020) lower in PRO (Δ: −0.25±1.10 pg/mL, p=0.453) compared to PL (Δ: +0.36 pg/mL, p=0.160).

The results obtained from this this embodiment indicate that 12-weeks of probiotic supplementation attenuated increases in TNF-α which were observed in the placebo group.

There were no other significant group differences in any other biochemical markers examined. However, a trend (F=3.41, p=0.078, $\eta^2$=0.134) for lower cortisol concentrations in PRO (Δ: −76.9±222.1 nmol/L, p=0.235) compared to PL (Δ: +39.6±126.03 nmol/L, p=0.300) was observed at POST. Collectively, significant increases were observed for testosterone (p=0.045), LN IL-10 (p=0.048), SIgA rate (p=0.031), and LN SIgM rate (p=0.002) following 12-weeks of offseason training across groups. No major effects over time were observed in any other biochemical marker.

While IL-10 concentrations in this embodiment did not differ between groups, significant elevations were seen as a result of the offseason training program.

No significant differences in testosterone (T), cortisol (C), or T:C ratio were observed between groups in this embodiment. Nevertheless, a trend was observed for decreased cortisol concentrations in the probiotic group.

Furthermore, coupled with the probiotic attenuation of TNF-α in our study, coinciding lower average cortisol levels in the probiotic group indicate a better homeostatic balance for health, recovery, and physiological adaptations.

In this embodiment, no significant differences were observed in plasma zonulin concentrations following our 12-week intervention.

Nevertheless, since no adverse effects of probiotic supplementation were observed, the findings of this embodiment provide additional support for the possible benefits of probiotic supplementation in an athletic population. Overall, during a time period where multiple stressors were present, probiotic supplementation may alter cytokine production, e.g. TNF-α, in male collegiate athletes.

Further, it is expected that probiotic supplementation using B. Subtilis, containing supplements as described herein will provide physical and/or physiological benefits in a human male population in conjunction with reduced TNF-α levels in serum.

In certain embodiments, the compositions comprising Bacillus subtilis can include one or more dry carriers selected from the group consisting of trehalose, maltodextrin, rice flour, microcrystalline cellulose, magnesium stearate, inositol, fructooligosaccharide, galactooligosaccharide, dextrose, and the like. In certain embodiments, the dry carrier can be added to the compositions comprising Bacillus subtilis in a weight percentage of from about 1% to about 95% by weight of the composition.

In certain embodiments, the compositions comprising Bacillus subtilis can include one or more liquid or gel-based carriers, selected from the group consisting of water and physiological salt solutions, urea, alcohols and derivatives thereof (e.g., methanol, ethanol, propanol, butanol), glycols (e.g., ethylene glycol, propylene glycol), and the like; natural or synthetic flavorings and food-quality coloring agents, all compatible with the organism; thickening agents selected from the group consisting of corn starch, guar gum, xanthan gum, and the like; one or more spore germination inhibitors selected from the group consisting of hyper-saline carriers, methylparaben, guargum, polysorbate, preservatives, and the like. In certain embodiments, the one or more liquid or gel-based carrier(s) can be added to the compositions comprising Bacillus subtilis in a weight/volume percentage of from about 0.6% to about 95% weight/volume of the composition. In certain embodiments, the natural or synthetic flavoring(s) can be added to the compositions comprising Bacillus subtilis in a weight/volume percentage of from about 3.0% to about 10.0% weight/volume of the composition. In certain embodiments, the coloring agent(s) can be added to the compositions comprising *Bacillus subtilis* in a weight/volume percentage of from about 1.0% to about 10.0% weight/volume of the composition. In certain embodiments, the thickening agent(s) can be added to the compositions comprising *Bacillus subtilis* in a weight/volume percentage of about 2% weight/volume of the composition. In certain embodiments, the one or more spore germination inhibitors can be added to the compositions comprising *Bacillus subtilis* in a weight/volume percentage of about 1% weight/volume of the composition.

Delivery System

Suitable dosage forms include tablets, capsules, solutions, suspensions, powders, gums, and confectionaries. Sublingual delivery systems include, but are not limited to, dissolvable tabs under and on the tongue, liquid drops, and beverages. Edible films, hydrophilic polymers, oral dissolvable films, or oral dissolvable strips can be used. Other useful delivery systems comprise oral or nasal sprays or inhalers, and the like. Suitable dosage forms include tablets, capsules, solutions, suspensions, powders, gums, and confectionaries. Sublingual delivery systems include, but are not limited to, dissolvable tabs under and on the tongue, liquid drops, and beverages. Edible films, hydrophilic polymers, oral dissolvable films, or oral dissolvable strips can be used. Other useful delivery systems comprise oral or nasal sprays or inhalers, and the like.

For oral administration, probiotics may be further combined with one or more solid inactive ingredients for the preparation of tablets, capsules, pills, powders, granules, or other suitable dosage forms. For example, the active agent may be combined with at least one excipient selected from the group consisting of fillers, binders, humectants, distintegrating agents, solution retarders, absorption accelerators, wetting agents, absorbents, and lubricating agents. Other useful excipients include, but are not limited to, magnesium stearate, calcium stearate, mannitol, xylitol, sweeteners, starch, carboxymethylcellulose, microcrystalline cellulose, silica, gelatin, silicon dioxide, and the like.

In certain embodiments, the components of compositions administered according to the methods of the present disclosure, together with one or more conventional adjuvants, carriers, or diluents, may thus be placed into the form of pharmaceutical compositions and unit dosages thereof. Such forms include: solids, and in particular, tablets, filled capsules, powder and pellet forms; liquids, and in particular, aqueous or non-aqueous solutions, suspensions, emulsions, elixirs; and capsules filled with the same; all for oral use, suppositories for rectal administration, and sterile injectable solutions for parenteral use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

The components of the compositions administered according to the methods of the present disclosure can be administered in a wide variety of oral and parenteral dosage forms. It will be obvious to those skilled in the art that the following dosage forms may comprise, in certain embodiments, as the active component, either a chemical compound of the present disclosure or a pharmaceutically acceptable salt of a chemical compound of the present disclosure.

For preparing pharmaceutical compositions to be administered according to the methods of the present disclosure, pharmaceutically acceptable carriers can be either solid or liquid. Solid form preparations include powders, tablets, pills, capsules, cachets, suppositories, and dispersible granules. A solid carrier can be one or more substances that may also act as diluents, flavoring agents, solubilizers, lubricants, suspending agents, binders, preservatives, tablet disintegrating agents, or encapsulating materials.

In powders, the carrier is a finely divided solid, which is in a mixture with the finely divided active component. In tablets, the active component is mixed with the carrier having the necessary binding capacity in suitable proportions and compacted in the shape and size desired.

In certain embodiments, powders and tablets administered according to methods of the present disclosure preferably may contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without additional carriers, is surrounded by a carrier, which is thus in association with it. Similarly, cachets and lozenges are included. Tablets, powders, capsules, pills, cachets, and lozenges are included. Tablets, powders, capsules, pills, cachets, and lozenges can be used as solid forms suitable for oral administration.

Liquid preparations include, but are not limited to, solutions, suspensions, and emulsions, for example, water or water-propylene glycol solutions. For example, parenteral injection liquid preparations can be formulated as solutions in aqueous polyethylene glycol solution. In certain embodiments, chemical compounds administered according to methods of the present disclosure may thus be formulated for parenteral administration (e.g., by injection, for example, bolus injection or continuous infusion) and may be presented in unit dose for administration in ampoules, pre-filled syringes, small-volume infusion, or in multi-dose containers with an added preservative. The compositions may take such forms as suspensions, solutions, or emulsions in oily or aqueous vehicles, and may contain formulation agents such as suspending, stabilizing, and/or dispersing agents. Alternatively, the active ingredient may be in powder form, obtained by aseptic isolation of sterile solid or by lyophilization from solution, for constitution with a suitable vehicle, e.g., sterile, pyrogen-free water, before use.

Aqueous solutions suitable for oral use can be prepared by dissolving the active component in water and adding suitable colorants, flavors, stabilizing and thickening agents, as desired. Aqueous suspensions suitable for oral use can be made by dispersing the finely divided active component in water with viscous material, such as natural or synthetic gums, resins, methylcellulose, sodium carboxymethylcellulose, or other well-known suspending agents.

Compositions suitable for topical administration in the mouth include, but are not limited to: lozenges comprising the active agent in a flavored base, usually sucrose and acacia or tragacanth; pastilles comprising the active ingredient in an inert base such as gelatin and glycerine or sucrose and acacia; and mouthwashes comprising the active ingredient in suitable liquid carrier.

Solutions or suspensions are applied directly to the nasal cavity by conventional means, for example, with a dropper, pipette, or spray. The compositions may be provided in single or multi-dose form. In compositions intended for administration to the respiratory tract, including intranasal compositions, the compound will generally have a small particle size, for example, of the order of 5 microns or less. Such a particle size may be obtained by means known in the art, for example, by micronization.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself; or it can be the appropriate number of any of these in packaged form.

Tablets, capsules, and lozenges for oral administration and liquids for oral use are preferred compositions. Solutions or suspensions for application to the nasal cavity or to the respiratory tract are preferred compositions. Transdermal patches for topical administration to the epidermis are preferred.

Further details on techniques for formulation and administration may be found in the latest edition of REMINGTON'S PHARMACEUTICAL SCIENCES (Mack Publishing Co., Easton, PA).

Routes of Administration

The compounds may be administered by any route, including, but not limited to, oral, sublingual, buccal, ocular, pulmonary, rectal, and parenteral administration, or as an oral or nasal spray (e.g., inhalation of nebulized vapors, droplets, or solid particles). Parenteral administration includes, for example, intravenous, intramuscular, intraarterial, intraperitoneal, intranasal, intravaginal, intravesical (e.g., to the bladder), intradermal, transdermal, topical, or subcutaneous administration. Also contemplated within the scope of the invention is the instillation of a pharmaceutical composition in the body of the patient in a controlled formulation, with systemic or local release of the drug to occur at a later time. For example, the drug may be localized in a depot for controlled release to the circulation, or for release to a local site.

Pharmaceutical compositions of the invention may be those suitable for oral, rectal, bronchial, nasal, pulmonal, topical (including buccal and sub-lingual), transdermal, vaginal or parenteral (including cutaneous, subcutaneous, intramuscular, intraperitoneal, intravenous, intraarterial, intracerebral, intraocular injection, or infusion) administration, or those in a form suitable for administration by inhalation or insufflation, including powders and liquid aerosol administration, or by sustained release systems. Suitable examples of sustained release systems include semipermeable matrices of solid hydrophobic polymers containing the compound of the invention, which matrices may be in the form of shaped articles, e.g., films or microcapsules.

The use of the terms "a," "an," "the," and similar referents in the context of describing the present invention (especially in the context of the claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. Use of the term "about" is intended to describe values either above or below the stated value in a range of approximately ±10%; in other embodiments, the values may range in value above or below the stated value in a range of approximately ±5%; in other embodiments, the values may range in value above or below the stated value in a range of approximately ±2%; in other embodiments, the values may range in value above or below the stated value in a range of approximately ±1%. The preceding ranges are intended to be made clear by context, and no further limitation is implied. All methods described herein can be performed in any suitable order unless otherwise indicated here in or otherwise clearly contradicted by context. The use of any and all examples, or exemplary language (e.g., "such as") provided herein, is intended merely to better illuminate the invention and does not pose a limitation on the scope of the invention unless otherwise stated. No language in the specification should be construed as indicating any non-claimed element as essential to the practice of the invention.

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

All references cited herein are incorporated by reference in their entireties. The present invention may be embodied in other specific forms without departing from the spirit or essential attributes thereof, and, accordingly, reference should be made to the appended claims, rather than to the foregoing specification, as indicating the scope of the invention.

We claim:

1. A method of reducing tumor necrosis factor-alpha (TNF-α) in human serum, comprising the steps of:
   (a) administering orally to a human a composition comprising an isolated strain of *Bacillus subtilis* subspecies *inaquosorum* having accession number NRRL B-67989 in a dose of from about $1 \cdot 10^8$ colony forming units (CFU) per day to about $1 \cdot 10^{11}$ CFU per day for about 12 weeks; and
   (b) submitting the human to a resistance training program throughout the 12 weeks.

2. The method of claim 1, wherein the resistance program includes workouts 2-3 times per week.

3. The method of claim 1, further comprising the steps of measuring TNF-α in blood plasma of the human both before and after steps (a) and (b).

4. The method of claim 1, wherein the composition comprises the isolated strain of *Bacillus subtilis* in a dose of from about $1 \cdot 10^9$ CFU per day to about $1 \cdot 10^{10}$ CFU per day.

5. The method of claim 4, wherein the TNF-α level is reduced by about 0.2 pg/mL in serum.

6. A method for treating or reducing inflammation in a human, comprising the steps of:
   (a) administering orally to the human in need of such treatment a composition comprising an isolated strain of *Bacillus subtilis* subspecies *inaquosorum* having accession number NRRL B-67989 in a dose of from about $1 \cdot 10^8$ CFU per day to about $1 \cdot 10^{11}$ CFU per day for about 12 weeks, and
   (b) measuring TNF-α in blood plasma of the human, wherein the TNF-α level is reduced in serum.

7. The method of claim 6, further comprising the step of submitting the human to a resistance training program throughout the 12 weeks of step (a).

8. The method of claim 6, wherein the composition comprises the isolated strain of *Bacillus subtilis* in a dose of from about $1 \cdot 10^9$ CFU per day to about $1 \cdot 10^{10}$ CFU per day.

9. The method of claim 7, wherein the composition comprises the isolated strain of *Bacillus subtilis* in a dose of from about $1 \cdot 10^9$ CFU per day to about $1 \cdot 10^{10}$ CFU per day.

10. The method of claim 9, wherein the resistance program includes workouts 2-3 times per week.

11. The method of claim 10, further comprising the step of measuring TNF-$\alpha$ in blood plasma of the human before step (a).

12. The method of claim 11, wherein the TNF-$\alpha$ level is reduced by about 0.2 pg/mL in serum.

\* \* \* \* \*